United States Patent
Fiebelkorn et al.

(10) Patent No.: US 6,651,484 B2
(45) Date of Patent: Nov. 25, 2003

(54) DEVICE FOR MEASURING THE SPECIFIC DENSITY OF A GASEOUS OR LIQUID MEDIUM

(75) Inventors: Klaus-Dieter Fiebelkorn, Minfeld (DE); Alf Puettmer, Karlsruhe (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/103,828

(22) Filed: Mar. 25, 2002

(65) Prior Publication Data
US 2003/0005748 A1 Jan. 9, 2003

Related U.S. Application Data

(63) Continuation of application No. PCT/DE00/03294, filed on Sep. 21, 2000.

(30) Foreign Application Priority Data
Sep. 23, 1999 (DE) ...................................... 299 16 826 U

(51) Int. Cl.⁷ ................................................ G01N 1/00
(52) U.S. Cl. ...................................... 73/32 A; 310/336
(58) Field of Search .............................. 73/32 A, 32 R, 73/597, 629; 310/336

(56) References Cited

U.S. PATENT DOCUMENTS

| | | | | |
|---|---|---|---|---|
| 2,602,101 A | * | 7/1952 | Mesh | 310/336 |
| 3,393,331 A | * | 7/1968 | Puckett | 310/336 |
| 3,555,880 A | * | 1/1971 | Menius et al. | 73/32 A |
| 4,297,608 A | * | 10/1981 | Jensen | 310/335 |
| 4,991,124 A | * | 2/1991 | Kline | 702/50 |
| 6,247,354 B1 | * | 6/2001 | Vig et al. | 73/54.41 |

FOREIGN PATENT DOCUMENTS

| | | |
|---|---|---|
| DE | 30 16 323 A1 | 11/1980 |
| DE | 195 35848 C1 | 7/1996 |
| DE | 195 35 846 A1 | 3/1997 |
| EP | 0 364 168 A2 | 4/1990 |
| EP | 0 482 326 B1 | 4/1992 |
| EP | 0 483 491 B1 | 5/1992 |
| EP | 0 527 651 A1 | 2/1993 |
| JP | 01060657 | 3/1989 |

* cited by examiner

Primary Examiner—Hezron Williams
Assistant Examiner—John Hanley
(74) Attorney, Agent, or Firm—Sughrue Mion, PLLC

(57) ABSTRACT

A device for measuring the specific density of a gaseous or liquid medium (8) having an acoustic transducer (1), which is active on both sides, and further having cylindrical delay paths (4, 5) as well as a ring (6) in which the acoustic transducer (1) is embedded. The diameter of the acoustic transducer (1) is selected such that it is smaller than the diameter of the delay paths (4, 5) so that diffracted waves generated in the area of the edge of the acoustic transducer generate fewer parasitic echoes and surface waves on the boundary surfaces (7, 9) resulting in less corruption of the measured result.

15 Claims, 1 Drawing Sheet

DEVICE FOR MEASURING THE SPECIFIC DENSITY OF A GASEOUS OR LIQUID MEDIUM

This is a Continuation of International Application PCT/DE00/03294, with an international filing date of Sep. 21, 2000, which was published under PCT Article 21(2) in German, and the disclosure of which is incorporated into this application by reference.

FIELD OF AND BACKGROUND OF THE INVENTION

The invention relates generally to a device and method for measuring the specific density of a gaseous or liquid medium. More specifically, the invention relates to a device in which an acoustic transducer is provided and the transducer is excited to emit acoustic pulses and acoustic signals reflected through the medium to be measured and through a reference medium are compared to determine the desired characteristics of the medium to be measured.

German Patent Number DE 195 35 848 C1, which is incorporated herein by reference for all it teaches, discloses a device for measuring the acoustic impedance of liquid media using a multilayer acoustic transducer arrangement. An acoustic transducer simultaneously injects an acoustic pulse into a first and a second acoustic delay path, respectively. The acoustic transducer receives, and an evaluation device evaluates, the acoustic waves reflected at a boundary layer between the first delay path and a medium to be inspected as well as the acoustic waves reflected at a boundary layer between the second delay path and a reference medium. The ratio of the amplitudes of the two received acoustic pulses can be used to determine the acoustic impedance or the specific density of the measured medium. The two acoustic delay paths are essentially cylindrical in shape. A disk-shaped acoustic transducer of the same diameter is arranged between the two bases of the cylindrical delay paths.

One drawback of the prior art device described above is that so-called diffracted waves that are generated in the area of the edge of the disk-shaped acoustic transducer cause parasitic echoes in the delay paths, which are superimposed on the measurement signal and reduce the signal-to-noise ratio. In addition, the refracted waves excite surface waves on the bases of the delay paths, which also limit the accuracy of the measurement. Another drawback of the prior art device is that the acoustic transducer, which is embodied as a disk-shaped piezo-ceramic element, is subject not only to axial mode vibrations, which are desired for the measurement, but also the acoustic transducer freely vibrates in radial mode. These additional drawbacks further diminish the accuracy of the measurement.

OBJECTS OF THE INVENTION

To address the deficiencies in the prior art device described above, as well as other disadvantages of other prior art devices, an object of the present invention is to provide a device for measuring the specific density of a gaseous or liquid medium with improved measuring accuracy.

SUMMARY OF THE INVENTION

To attain this and other objects, a device used in the measurement of the specific density of a gaseous or liquid medium is proposed, the device having an acoustic transducer active on both of two sides and being operable to emit and receive acoustic signals. At least two substantially cylindrical acoustic delay paths, each having a respective known acoustic impedance, are provided, where one of the delay paths is arranged on one of the two sides of the acoustic transducer and on its base, facing away from the acoustic transducer, this delay path has a first boundary surface to the medium to be measured. Further, a second delay path is arranged on the other of the two sides of the acoustic transducer and on its base, facing away from the acoustic transducer, the second delay path has a second boundary surface to a reference medium whose characteristics are known. The acoustic transducer has a smaller diameter than the bases of the delay paths and the acoustic transducer is inserted into a substantially hollow cylindrical ring, an inside diameter of which is adapted to an outside diameter of the acoustic transducer and an outside diameter of which is adapted to the diameter of the bases of the delay paths.

In accordance with the present invention, due to a smaller diameter of the acoustic transducer compared to the diameter of cylindrical delay paths, diffracted waves produce fewer and weaker parasitic echoes in the delay paths, and the strength of the surface waves on the bases of the delay paths is reduced. A ring into which the acoustic transducer is inserted dampens the radial vibrations of the acoustic transducer. A further advantage according to the present embodiment results from the robust construction of the device, which is realized by the addition of the ring, since the forces acting between the delay paths can be absorbed by the ring and do not affect the boundary surfaces between the acoustic transducer and the delay paths.

The outside diameter of the acoustic transducer is preferably selected to be between one quarter and three quarters of the diameter of the bases of the delay paths. This dimensioning has the advantages that the acoustic transducer emits a substantially flat wave front into the delay paths and sufficient acoustic energy for the measurement is produced.

Since the acoustic transducer is embedded in the ring between the two delay paths in a positive fit, it is important that the thermal expansion coefficients of the employed materials be approximately equal. If the thermal expansion coefficients are approximately equal, thermal stresses created within the device under fluctuating temperatures are relatively low and the required long-term stability of the acoustic coupling of the components is achieved. It is, therefore, advantageous to embody the acoustic transducer as, for example, a piezo-ceramic element and to make the two delay paths, and the ring, of quartz glass or Zerodur.

The electrodes of the acoustic transducer can be produced by vacuum coating the bases of the delay paths facing the acoustic transducer. The vacuum coating technique has the advantage that the electrodes can be extended up to the lateral surfaces of the delay paths and can be readily contacted at that location.

According to another embodiment, an electrically conductive adhesive, particularly an electrically conductive epoxy resin adhesive, can be used to bond the bases of the delay paths facing the acoustic transducer. This eliminates the vacuum coating step of the delay paths, since the adhesive can perform the function of the electrodes of the acoustic transducer. In this embodiment as well, the electrodes can be easily extended up to the lateral surfaces, so that the device as a whole can be cost-effectively produced.

Another low-cost process for producing the electrodes involves the application of a metal foil to metallize the respective base.

BRIEF DESCRIPTION OF THE DRAWINGS

The invention as well as some embodiments and advantages will now be described in greater detail with reference to the drawing, which depicts an exemplary embodiment of the invention.

DETAILED DESCRIPTION OF THE PREFERRED EMBODIMENTS

Figure 1:
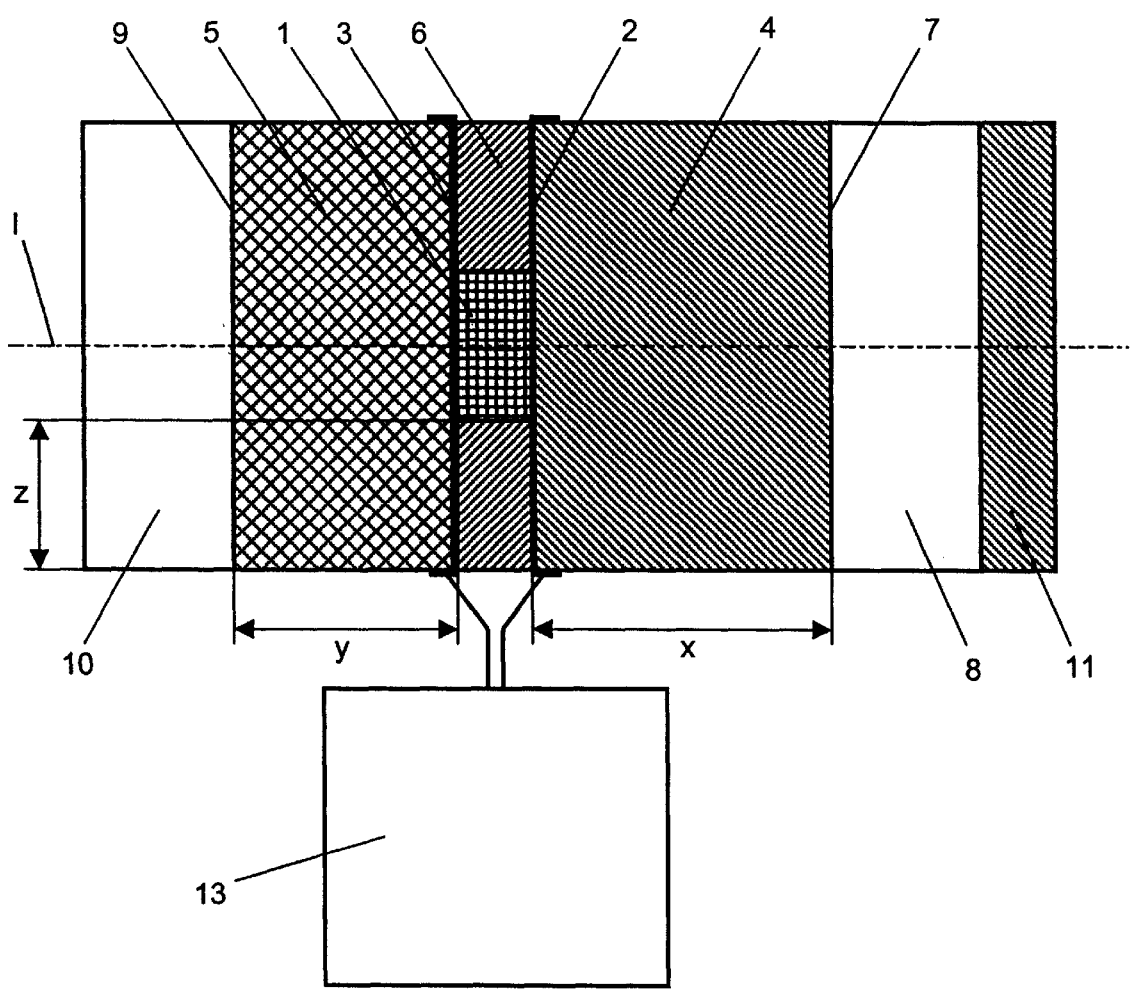
FIG. 1 is a diagram illustrating an embodiment in accordance with the present invention.

Referring to the embodiment shown in FIG. 1, a disk-shaped acoustic transducer 1, comprising, for example, a piezo-ceramic element having two electrodes 2 and 3 arranged on the bases thereof, is disposed between a first delay path 4 and a second delay path 5. The two delay paths 4 and 5 are made of, for example, quartz glass and are cylindrical. The bases of delay paths 4 and 5, which carry vapor-deposited metal electrodes 2 and 3, are permanently bonded using an epoxy resin adhesive on the two bases of a hollow cylindrical ring 6. Ring 6 encloses the acoustic transducer 1 in form-fit manner and is likewise bonded to the lateral surface of the acoustic transducer 1.

A base 7 of the delay path 4, facing away from the acoustic transducer 1, forms a boundary surface to a medium 8 to be measured. An acoustic pulse emitted by the acoustic transducer 1 is reflected at boundary surface 7 as a function of the acoustic impedances of the first delay path 4 and the measured medium 8. A further boundary surface 9 is formed by the base of the second delay path 5 facing away from the acoustic transducer 1 and a reference medium 10. In this embodiment, the reference medium 10 is ambient air. A space enclosing the measured medium 8 is bounded by a wall 11, on which can be arranged an additional acoustic transducer operated as a receiver.

An evaluation unit 13 can be connected to the electrodes 2 and 3, which extend up to the lateral surfaces of the first delay path 4 and the second delay path 5, respectively. The evaluation unit 13 applies electrical pulses to the electrodes 2 and 3 to excite the acoustic transducer 1 and, in turn, receives and evaluates the electrical signals generated in the acoustic transducer 1 by the reflected acoustic waves. An example of such an evaluation unit 13 is disclosed in European Patent Application Number 0 364 168, which is incorporated herein by reference for all it teaches.

The parts depicted in the embodiment of FIG. 1 are rotationally symmetrical relative to an axis I. Also, as mentioned above, the two delay paths 4 and 5 as well as ring 6 are made of quartz glass. Quartz glass has approximately the same thermal expansion coefficient as the piezo-ceramic element of the acoustic transducer 1. Therefore, at most, low thermal stresses occur in the device. As a result, good long-term stability of the bonds is ensured. The forces acting between the two delay paths 4 and 5 are largely absorbed by ring 6 and thus affect the acoustic transducer 1 only to a minor extent. Accordingly, an overall robust construction of the device is achieved.

Height x of the first delay path 4 and height y of the second delay path 5 are preferably different from each other so that a time window for evaluating the signals produced in the acoustic transducer 1 by the reflected acoustic waves can be set in such a way that the fewest possible parasitic signals lie within the window and the acoustic wave reflected at boundary surface 7 and at boundary surface 9 can be independently measured. Thickness z of the wall of the hollow cylindrical ring 6 is preferably selected such that the signals caused by the boundary surfaces 7 and 9 can be distinguished from a radial parasitic signal generated at the outer lateral surface of ring 6 through a corresponding, suitable definition of the evaluation window.

As an alternative to the embodiment depicted in FIG. 1, electrodes 2 and 3 may be formed by application of a metal foil or by a conductive epoxy resin adhesive, so that vapor deposition of a metallization is not required.

The above description of certain embodiments of the present invention has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. A device for measuring the specific density of a gaseous or liquid medium, the device comprising:

an acoustic transducer that is active on both of two sides, said acoustic transducer being operable to emit and receive acoustic signals;

at least two substantially cylindrical acoustic delay paths, each having a respective known acoustic impedance, wherein a first of said delay paths is arranged on one of the two sides of the acoustic transducer and on its base, facing away from the acoustic transducer, the first delay path has a first boundary surface to the medium to be measured, and wherein a second of said delay paths is arranged on the other of the two sides of the acoustic transducer and on its base, facing away from the acoustic transducer, the second delay path has a second boundary surface to a reference medium; and a substantially hollow cylindrical ring;

wherein the acoustic transducer has a smaller diameter than the bases of the delay paths and the acoustic transducer is inserted into the substantially hollow cylindrical ring, an inside diameter of which is adapted to an outside diameter of the acoustic transducer and an outside diameter of which is adapted to the diameter of the bases of the delay paths.

2. A device as claimed in claim 1, further comprising an evaluation unit operable to evaluate electrical signals generated in the acoustic transducer.

3. A device as claimed in claim 1, wherein the outside diameter of the acoustic transducer is smaller than three quarters and larger than one quarter of the diameter of the bases of the delay paths.

4. A device as claimed in claim 1, wherein said acoustic transducer is a piezo-ceramic element, the delay paths and the ring are made of quartz glass or Zerodur, and the delay paths are bonded to the substantially hollow cylindrical ring.

5. A device as claimed in claim 4, wherein a metal is vapor deposited onto the bases of the delay paths facing the acoustic transducer.

6. A device as claimed in claim 4, wherein an electrically conductive adhesive bonds the bases of the delay paths facing the acoustic transducer.

7. A device as claimed in claim 6, wherein the electrically conductive adhesive is an epoxy resin adhesive.

8. A device as claimed in claim 4, wherein the bases of the delay paths facing the acoustic transducer are metallized by a metal foil applied thereto.

9. A method of measuring the specific density of a gaseous or liquid medium, the method comprising:

placing an acoustic transducer within a cylindrical ring;

providing a respective delay path material on each of two sides of the cylindrical ring, each delay path material having a respective boundary surface area adjacent to the acoustic transducer which is greater than a surface area of the respective side of the acoustic transducer on which the delay path material is provided;

placing respective electrodes between the cylindrical ring and each of the delay path materials;

placing a reference material adjacent to one of the delay path materials;

placing the medium to be measured adjacent to the other delay path material;

attaching an evaluation unit to the electrodes;

exciting the acoustic transducer by presenting the electrodes with electrical pulses from the evaluation unit; and determining the specific density of the medium to be measured by evaluating acoustic signals reflected through the medium to be measured and acoustic signals reflected through the reference material.

10. A method as claimed in claim 9, wherein an outer diameter of the acoustic transducer is between one-fourth and three-fourths a diameter of the delay path materials.

11. A method of forming a device for measuring the specific density of a gaseous or liquid medium, the method comprising:

placing an acoustic transducer within a cylindrical ring;

providing a respective delay path material on both of two sides of the cylindrical ring;

placing respective electrodes between the cylindrical ring and each of the delay path materials;

placing a reference material adjacent to one of the delay path materials;

placing the medium to be measured adjacent to the other of the two delay path materials; and wherein an outer diameter of the acoustic transducer is less than an outer diameter of the two delay path materials.

12. The method as claimed in claim 11, wherein the electrodes are formed by vapor-depositing a metal on respective boundaries between the cylindrical ring and the delay path materials and on at least a portion of respective outer sides of the delay path materials.

13. The method as claimed in claim 11, wherein respective heights of the delay path materials are different from one another.

14. The method as claimed in claim 11, wherein the cylindrical ring and the delay path materials are made from quartz glass or Zerodur.

15. The method as claimed in claim 11, wherein the acoustic transducer has an outer diameter between one-fourth and three-fourths a diameter of the delay path materials.

* * * * *